United States Patent
DiFoggio

(10) Patent No.: US 8,977,500 B2
(45) Date of Patent: Mar. 10, 2015

(54) DIELECTRIC SPECTROSCOPY FOR DOWNHOLE FLUID ANALYSIS DURING FORMATION TESTING

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 537 days.

(21) Appl. No.: 13/079,343

(22) Filed: Apr. 4, 2011

(65) Prior Publication Data

US 2011/0251795 A1 Oct. 13, 2011

Related U.S. Application Data

(60) Provisional application No. 61/323,582, filed on Apr. 13, 2010.

(51) Int. Cl.
*G06F 19/00* (2011.01)
*E21B 49/10* (2006.01)
*G01N 27/02* (2006.01)

(52) U.S. Cl.
CPC .............. *E21B 49/10* (2013.01); *G01N 27/026* (2013.01)
USPC .......................................................... 702/11

(58) Field of Classification Search
USPC .......................................................... 702/11
See application file for complete search history.

(56) References Cited

U.S. PATENT DOCUMENTS

| | | | |
|---|---|---|---|
| 4,009,434 A | 2/1977 | McKinlay | |
| 4,353,248 A | 10/1982 | Caldwell | |
| 4,626,773 A | 12/1986 | Kroeger et al. | |
| 4,774,471 A | 9/1988 | Sims | |
| 5,341,100 A | 8/1994 | Taylor | |
| 7,363,160 B2 | 4/2008 | Seleznev et al. | |
| 7,482,811 B2 | 1/2009 | Freedman | |
| 2003/0011386 A1* | 1/2003 | Xie et al. ...................... 324/694 |

OTHER PUBLICATIONS

Salinity—definition of salinity by the Free Online Dictionary, p. 1, Aug. 20, 2013.*
Tore Tjomsland, Jannicke Hilland, Alfred A. Christy, Johan Sjoblom, Mona Riis, Trond Friiso, Kjetil Folgero, "Comparison of infrared and impedance spectra of petroleum fractions," ELSEVIER, Fuel vol. 75 No. 3, pp. 322-332, 1996.
J. Ross MacDonald, "Impedance Sprectroscopy," Annals of Biomedical Engineering, vol. 20, pp. 289-305, 1992.
Agilent, "Solutions for Measuring Permittivity and Permeability with LCR Meters and Impedance Analyzers," Application Note 1369-1, Oct. 28, 2008.
James Barker, Eric J. Vanzura, William A. KissicK, "Improved Technique for Determining Complex Permittivity With the Transmission/Reflection Method," IEEE Transaction on Microwave Theory and Techniques, vol. 38, No. 8, Aug. 1990.

(Continued)

*Primary Examiner* — Tung S Lau
(74) *Attorney, Agent, or Firm* — Cantor Colburn LLP

(57) ABSTRACT

An apparatus for estimating a property of a downhole fluid, the apparatus includes: a carrier configured to be conveyed through a borehole penetrating the Earth; a downhole fluid extraction device disposed at the carrier and configured to extract the downhole fluid; and a dielectric spectrometer disposed at the carrier and configured to transmit electromagnetic energy into the extracted downhole fluid at a plurality of frequencies and to measure a plurality of responses to determine a permittivity of the extracted downhole fluid as a function of frequency; wherein the permittivity is used to estimate the property.

24 Claims, 4 Drawing Sheets

(56) References Cited

OTHER PUBLICATIONS

L. Jared West, David M. rippin, Tavi Murray, Heidy M. Mader, Bryn Hubbard, "Dielectric Permittivity Measurements on Ice Cores: Implication for Interpretation of Radar to yield Glacial Unfrozen Water Content," Journal of Environmental & Engineering Geophysics, Mar. 2007; v. 12; issue p. 37-45; DOI: 10.2113/JEEG12.1.37 [retrieved on Jun. 16, 2011]. Retrieved from the internet, URL: http://jeeg.geoscienceworld.org/cgi/content/abstract/12/1/37.

D. Healy, C. Katopodis, P. Tarrant, "Application of Ground Penetrating Radar for River Ice Surveys," CGU HS Committee on River Ice Processes and the Environment, 14th Workshop on the Hydraulics of Ice Cover Rivers, Quebec City, Jun. 19-22, 2007 [ retrieved on Jun. 16, 2011)]. Retrived from the Internet, URL: http://cripe.civil.ualberta.ca/Downloads/14th_Workshop/Healy-et-al-2007.pdf.

J. D. Hepburn, F. E. Vermeulen, F. S. Chute, "Resistivity of Nal-Glycerol Solutions," University of Alberta, Edmonton, Alberta, Canada, AIAA Journal, vol. 9, No. 11, p. 2270 [retrieved on Jun. 16, 2011]. Retrieved from the internet, URL: http://pdf.aiaa.org/jaPreview/AIAAJ/1971/PVJAPRE6498.pdf.

Martin Chaplin, "Water and Microwaves," Water structure and science, Sep. 24, 2009. [Retrieved on Jun. 16, 2011]. Retrieved from the internet, URL: http://www.lsbu.ac.uk/php-cgiwrap/water/pfp.php3?page=http://www.lsbu.ac.uk/water/microwave.html.

Ian Baker, "Studies in Natural Artificial Ice," Thayer School of Engineering at Dartmouth. [Retrieved on Jun. 16, 2011]. Retrieved from the internet, URL: http://engineering.dartmouth.edu/baker/ice.html.

G. Whittaker, "Microwave Heating Mechanisms," 1994 & 1997 [retrieved on Jun. 16, 2011]. Retrieved from the internet, URL: http://homepages.ed.ac.uk/ah05/ch1a.html.

Mike Willis, The Refractive Index of Water and Ice, May 5, 2007 [retrieved on Jun. 16, 2011]. Retrieved from the internet, URL: http://www.mike-willis.com/Tutorial/PF10.htm.

Nehager, "Broadband Dielectric Spectroscopy," Material Sensing & Instrumentation[retrieved on Jun. 16, 2011]. Retrieved from the internet, URL: http://www.msi-sensing.com/broadband_dielectrics.htm.

Robert K. Svec, Bulk and Surface Dielectric Dispersion of Water Ice, M.S. Geophysics Program Independent Study Report Submitted May 15, 1993[retrieved on Jun. 16, 2011]. Retrieved from the internet: URL: http://www.ees.nmt.edu/outside/gross/svec93.html.

Notification of Transmittal of the International Search Report and the Written Opinion of the International Searching Authority, or the Declaration; PCT/US2011/031877; Nov. 29, 2011.

* cited by examiner

DIELECTRIC SPECTROSCOPY FOR DOWNHOLE FLUID ANALYSIS DURING FORMATION TESTING

CROSS REFERENCE TO RELATED APPLICATIONS

This application claims the benefit of an earlier filing date from U.S. Provisional Application Ser. No. 61/323,582 filed Apr. 13, 2010, the entire disclosure of which is incorporated herein by reference.

BACKGROUND OF THE INVENTION

1. Field of the Invention

The present invention relates to apparatus and method for evaluating earth formations traversed by a well borehole and in particular to formation sampling and testing.

2. Description of the Related Art

Exploration and production of hydrocarbons require accurate and precise measurements of earth formations, which may contain reservoirs of the hydrocarbons. Accurate and precise measurements are important to enable efficient use of exploration and production resources.

Well logging is a technique used to perform measurements of an earth formation from within a borehole penetrating the formation. In well logging, a logging instrument or tool is conveyed through the borehole. The logging instrument performs the measurements from within the borehole at various depths. The measurements are associated with the depth at which the measurements were performed to create a log. In one embodiment, a wireline is used to support the logging instrument and to transmit measurements to the surface of the earth for processing and recording.

Many types of measurements can be made of the earth formation. In one type of measurement, a formation tester extracts a sample of a fluid from the formation. The fluid is then analyzed to determine a property of the fluid. In prior art tools, the fluid is illuminated with light and light reflected from the sample or transmitted through the sample is measured to determine the property. The light response is detected and converted to an electrical signal using a photodetector. Unfortunately, the environment deep within the borehole can have temperatures high enough to cause typical photodetectors, such as photodiodes, to respond poorly or fail entirely.

Therefore, what are needed are techniques to test a formation fluid and provide an accurate response in the high temperatures of a borehole environment.

BRIEF SUMMARY OF THE INVENTION

Disclosed is an apparatus for estimating a property of a downhole fluid, the apparatus includes: a carrier configured to be conveyed through a borehole penetrating the Earth; a downhole fluid extraction device disposed at the carrier and configured to extract the downhole fluid; and a dielectric spectrometer disposed at the carrier and configured to transmit electromagnetic energy into the extracted downhole fluid at a plurality of frequencies and to measure a plurality of responses to determine a permittivity of the extracted downhole fluid as a function of frequency; wherein the permittivity is used to estimate the property.

Also disclosed is a method for estimating a property of a downhole fluid, the method includes: conveying a carrier through a borehole penetrating the Earth; extracting the downhole fluid from within the Earth using a downhole fluid extraction device disposed at the carrier; determining a permittivity of the extracted downhole fluid as a function of frequency using a dielectric spectrometer disposed at the carrier and configured to transmit electromagnetic energy into the extracted downhole fluid at a plurality of frequencies and to measure a plurality of responses comprising electromagnetic energy due to the transmitting to measure the permittivity; and using the permittivity to estimate the property.

Further disclosed is a computer-readable storage medium comprising computer-executable instructions for estimating a property of a downhole fluid by implementing a method includes: transmitting electromagnetic energy into the downhole fluid at a plurality of frequencies; measuring a plurality of responses comprising electromagnetic energy due to the transmitting to determine a permittivity of the fluid as a function of frequency; and using the permittivity to estimate the property.

BRIEF DESCRIPTION OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings, wherein like elements are numbered alike, in which:

DETAILED DESCRIPTION OF THE INVENTION

Figure 1:
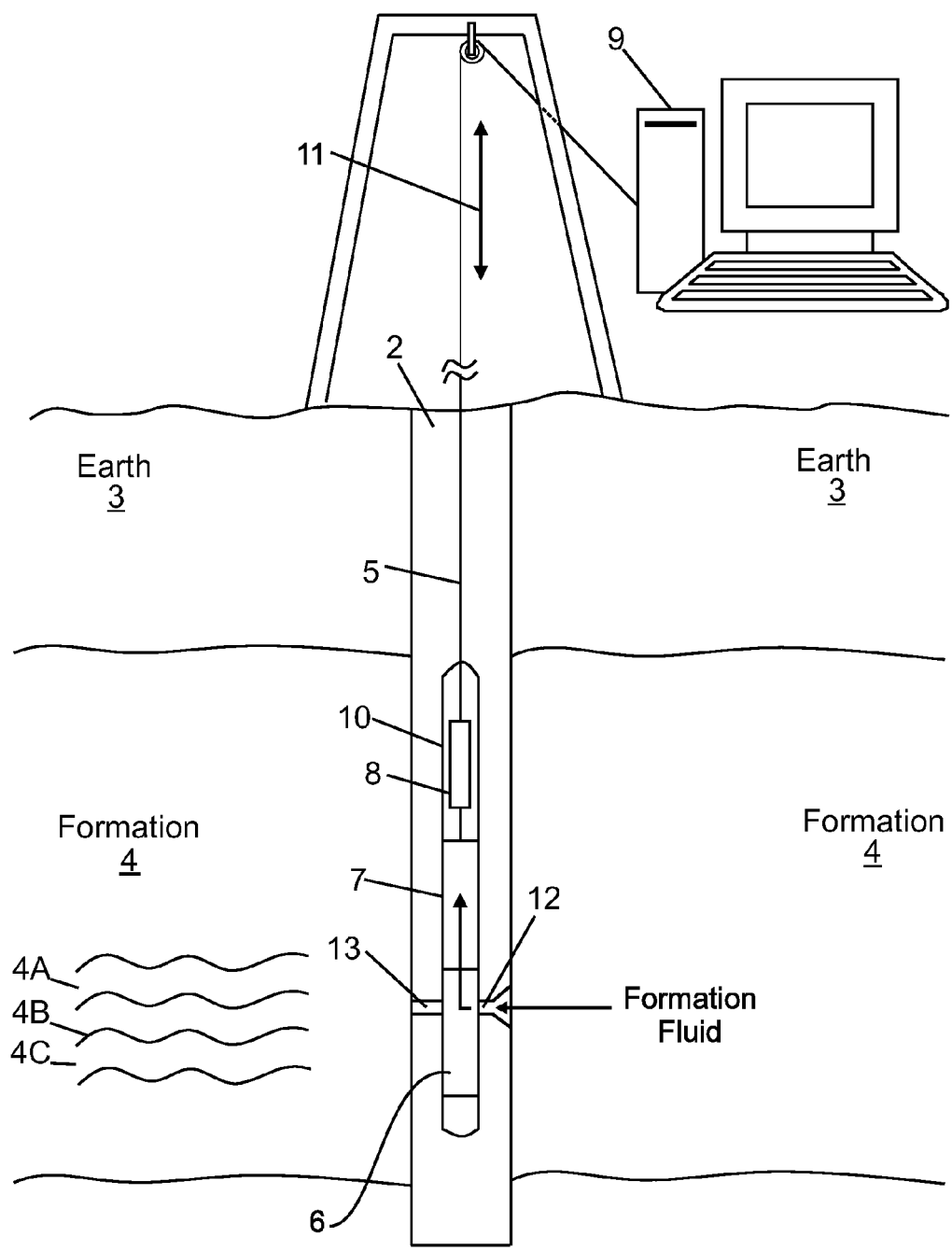
FIG. 1 illustrates an exemplary embodiment of a logging tool disposed in a borehole penetrating the earth.

Disclosed are exemplary embodiments of techniques for estimating a property of a fluid in an earth formation. The techniques, which include apparatus and method, call for conveying a logging tool in a borehole penetrating the earth formation. The logging tool is used to extract a sample of the fluid through the borehole wall. Upon obtaining the sample, the logging tool measures a permittivity (also referred to as a dielectric constant) of the fluid as a function of frequency using a dielectric spectrometer. The permittivity as a function of frequency is then used to estimate the property.

Permittivity is a measure of the ability of a material to polarize in response to an electric field and, thereby, reduce the total electric field inside the material. In addition, the permittivity of a material is a quantity used to describe the material's dielectric properties that influence reflection of electromagnetic waves at interfaces and the attenuation of wave energy within the material. Hence, in a non-limiting embodiment, the permittivity of a material can be determined by measuring the polarization of the material in response to an applied electric field or, in another non-limiting embodiment, by measuring reflection of electromagnetic waves by the material and wave energy dissipation in the material.

The permittivity, in the frequency domain, is generally a complex number and can be measured in several ways. One way is to apply an alternating current or field (AC) voltage to the sample using two electrodes that form a configuration similar to that of a capacitor. The resulting electrical current flowing through the sample is measured. The permittivity is then derived from the in-phase current and the out-of-phase current. The frequency of the applied voltage is generally in the radio-frequency range and, thus, it avoids the need for a typical optical photodetector with its inherent disadvantages in a high-temperature environment.

Another way to measure permittivity is to dispose the sample in a waveguide and subject the sample to radio-frequency (RF) electromagnetic (EM) waves emitted from a transducer or antenna. The resulting EM waves reflected by the sample and transmitted through the sample are measured. From the reflected EM wave measurements and the transmitted EM wave measurements, the permittivity of the sample can be derived.

A wide range of molecules and atoms can make up a formation fluid. These molecules and atoms can have polar structures, which are affected by electric fields. In general, the polar structures can have different masses and structures that are affected uniquely by AC electromagnetic energy of a certain frequency transmitted into the formation fluid. Examples of responses of the atoms and/or molecules include vibration, rotation, displacement, and dipole inducement. The frequency dependence results from the formation fluid not responding instantaneously to the applied electric field, but responding as a function of time. Hence, the chemical composition of the formation fluid can be identified by transmitting electromagnetic energy into the sample of the fluid at a plurality of frequencies and measuring resulting responses. In particular, the magnitude and/or phase of a response may be increased at a resonant frequency and the chemical composition can be identified by determining the frequencies where the resonances occur.

Because a response includes detecting electric or electromagnetic energy having a magnitude and phase with respect to the transmitted electromagnetic energy, the permittivity is represented as a complex number having a real component (i.e., the dielectric constant) and an imaginary component. In one embodiment, the real component relates to energy stored within the formation fluid when the fluid is exposed to an electric field and the imaginary component relates to the dissipation of energy (i.e., absorption and attenuation) within the formation fluid. Equation (1) provides a mathematical representation of permittivity "e" as a complex number where e' represents the real component, e'' represents the imaginary component, and $\omega$ is the angular frequency.

$$e(\omega)=e'(\omega)+i\,e''(\omega) \qquad (1)$$

Equation (1) may be rewritten as equation (2) where $D_0$ is the magnitude of the electric displacement field, $E_0$ is the magnitude of the electric field, and $\delta$ is the phase difference between $D_0$ and $E_0$.

$$e(\omega)=(D_0/E_0)(\cos\delta+i\sin\delta) \qquad (2)$$

Non-limiting embodiments of formation fluids of interest to petro-analysts include oil, water, and natural gas. Natural gas is composed almost entirely of nonpolar compounds (e.g., methane, ethane, propane, butane, etc.) and has few if any polar compounds such as asphaltenes. In crude oils, here are many polar compounds, especially asphaltenes, which lead to dielectric dispersions (i.e., changes in dielectric constant with frequency). For crude oils, the magnitude of the peak of the imaginary component e'' of permittivity, generally 1.8 to 2.0, over a frequency range of 1 MHz to 100 MHz is an indication of the amount of asphaltenes in the crude oil. Thus, by measuring the amount of asphaltenes in a sample of crude oil, the quality of the sample can be classified as light, medium or heavy oil. Use of higher frequencies such as 1 GHz can allow easy discrimination of oil (with a dielectric constant of approximately 2) compared to water (with a dielectric constant of approximately 80). By detecting changes in the chemical identity of the formation fluid with depth, a location of a boundary between formation layers can be identified.

For convenience, certain definitions are now presented. The term "radio-frequency" relates to frequencies below frequencies of light such that a photodetector is not required for detection or quantification of a received signal in the frequency range of interest. The term "dielectric spectrometer" relates to apparatus for measuring a dielectric constant of a formation fluid by transmitting electromagnetic energy into the fluid at a plurality of frequencies in order to determine the dielectric constant as a function of frequency. The frequencies are in a range of frequencies that correlate to resonances of materials that may be expected to be present in the fluid.

Reference may now be had to FIG. 1 illustrating an exemplary embodiment of a logging tool 10 disposed in a borehole 2 penetrating the Earth 3. The Earth 3 includes an earth formation 4 that includes layers 4A-4C, each layer having a property distinguishable from the property of another layer. As used herein, the term "formation" includes any subsurface materials of interest that may be analyzed to estimate a property thereof. The logging tool 10 is supported and conveyed through the borehole 2 by an armored cable 5 in a technique referred to as wireline logging. In addition to supporting the logging tool 10, the wireline 5 can be used to communicate information between the logging tool 10 and equipment at the surface of the Earth 3. In another technique referred to as logging-while-drilling (LWD), the logging tool 10 is disposed at a drill string or coiled tubing and is conveyed through the borehole 2 while the borehole 2 is being drilled. In LWD, the logging tool 10 performs a measurement during a temporary halt in drilling.

Still referring to FIG. 1, the logging tool 10 includes a formation fluid extraction device 6. The formation fluid extraction device 6 is configured to extract a sample of a fluid from the formation 4 through the wall of the borehole 2. The sample is then provided to a dielectric spectrometer 7 coupled to the fluid extraction device 6. The dielectric spectrometer 7 is configured to measure the dielectric constant or permittivity (i.e., real and complex parts) of the sample as a function of frequency to determine the resonant frequencies of the sample and, thus, the chemical identity of the materials in the sample. In one embodiment, the dielectric spectrometer 7 performs measurements with electromagnetic energy at a plurality of frequencies on one batch of a sample at a time. In another embodiment, the dielectric spectrometer 7 performs measurements with electromagnetic energy at a plurality of frequencies on a continuous flow of the extracted sample. When dielectric constant measurements are performed on a continuous flow of the sample, the flow rate is selected so that the composition of the sample is not expected to change significantly during the time interval in which the electromagnetic energy is transmitted at the plurality of frequencies.

Still referring to FIG. 1, the formation fluid extraction device 6 includes a probe 12 configured to extend from the device 6 and form a seal to the wall of the borehole 2. In order to keep the device 6 in place while the seal is being formed, the device 6 includes a brace 13 configured to extend from the device 6 and contact the wall of the borehole 2 opposite of the location where the seal is being formed. After the seal is formed, pressure within the probe 12 is reduced to extract the fluid from the formation 4 into the device 6 from which it can be transferred to the dielectric spectrometer 7.

Still referring to FIG. 1, the logging tool 10 includes a downhole electronics unit 8. The downhole electronics unit 8 can be configured to operate the logging tool 10 and/or communicate data 11 between the logging tool 10 and a surface-processing unit 9.

Figure 2:
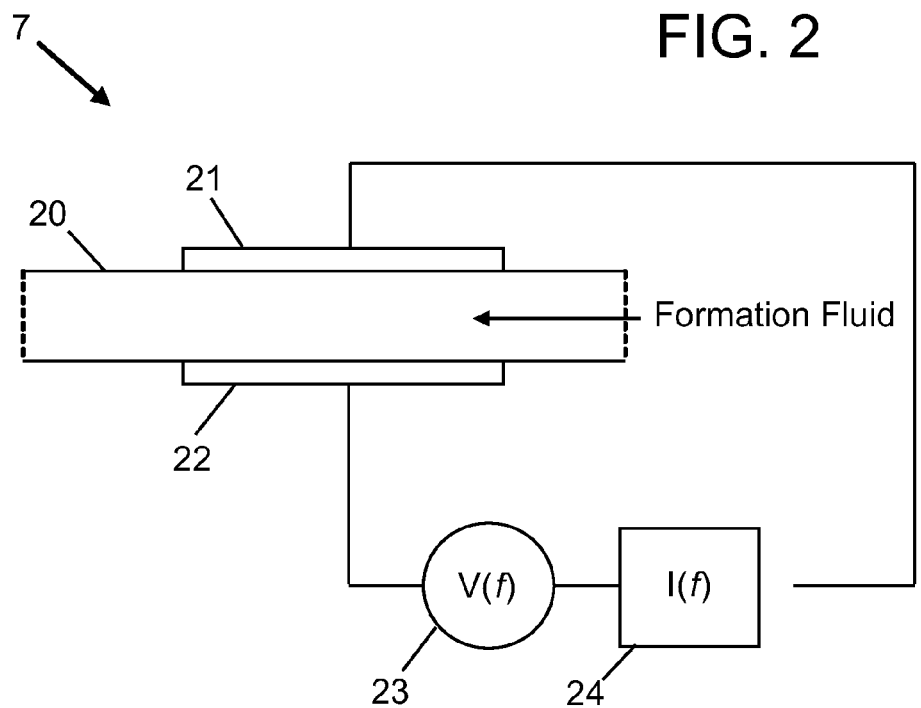
FIG. 2 depicts aspects of a dielectric spectrometer disposed at the logging tool.

Reference may now be had to FIG. 2 depicting aspects of one embodiment of the dielectric spectrometer 7. The dielectric spectrometer 7 includes a receiver 20 (also referred to as a test cell) configured to receive the sample of the formation fluid from the formation fluid extraction device 6. The receiver 20 includes a first electrode 21 and a second electrode 22 coupled to a variable frequency voltage source 23 configured to apply a voltage $V(\omega)$ to the electrodes 21,22 at a plurality of radio-frequencies. A current analyzer 24 measures the magnitude and phase of the current $I(\omega)$ flowing through the sample with respect to the applied voltage $V(\omega)$.

In one embodiment, the plurality of frequencies at which electromagnetic energy is transmitted into the sample includes a plurality of discrete frequencies. In another embodiment, the plurality of frequencies at which electromagnetic energy is transmitted into the sample is provided by a continuous sweep through a range of frequencies.

Figure 3:
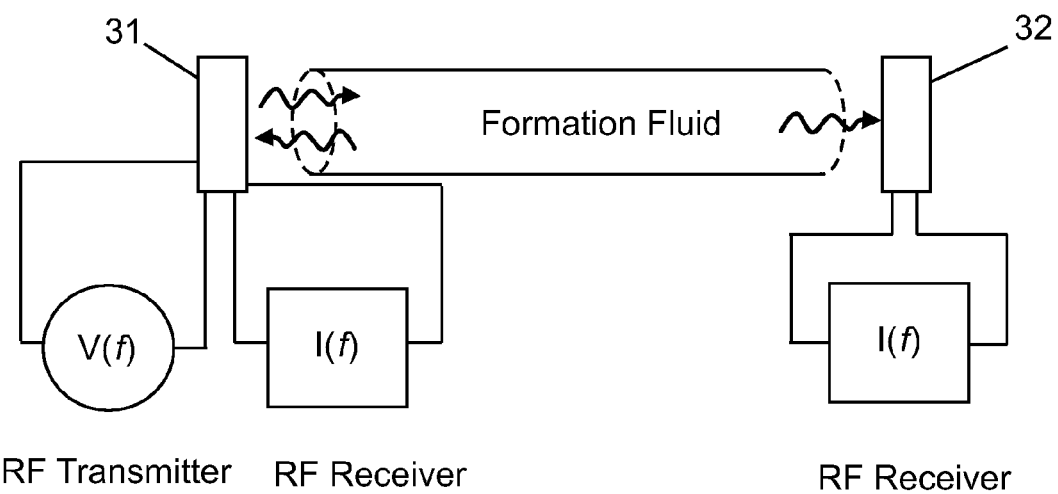
FIG. 3 depicts aspects of another dielectric spectrometer disposed at the logging tool.

Reference may now be had to FIG. 3 depicting aspects of another embodiment of the dielectric spectrometer 7. In this embodiment, the receiver 20 is a waveguide configured to hold the sample while receiving electromagnetic energy at a plurality of radio-frequencies from a first transducer 31. A second transducer 32 is configured to receive electromagnetic energy passing through the sample. A third transducer or the first transducer 31 in a receiving mode can be configured to receive electromagnetic energy reflected by the sample. Using magnitudes and phase relationships of the transmitted-to-sample, reflected-from-sample, and transmitted-through-sample electromagnetic energy, the dielectric constant as a function of frequency can be determined. Exemplary embodiments of the transducers 31 and 32 include antennas or coils.

Figure 4:
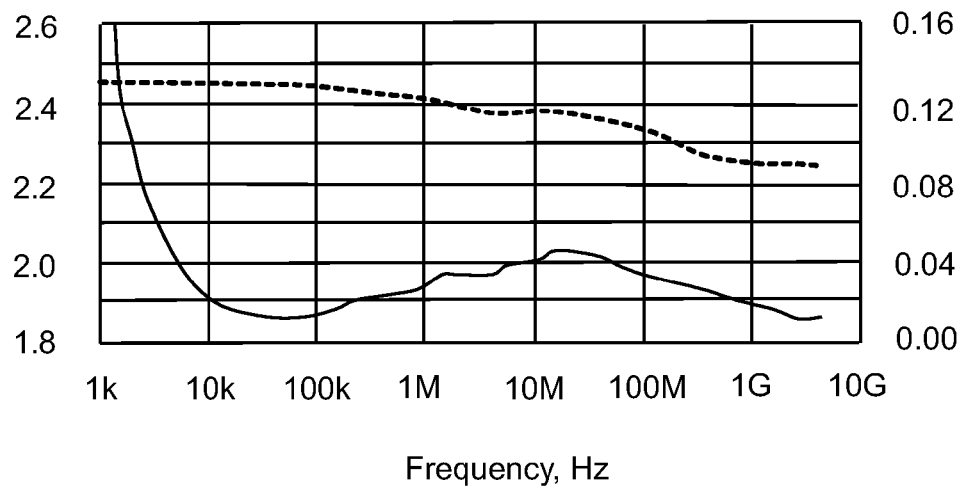
FIG. 4 illustrates an example of permittivity as a function of frequency for one type of oil.

Reference may now be had to FIG. 4 illustrating an example of permittivity as a function of frequency of one grade of oil.

Figure 5:
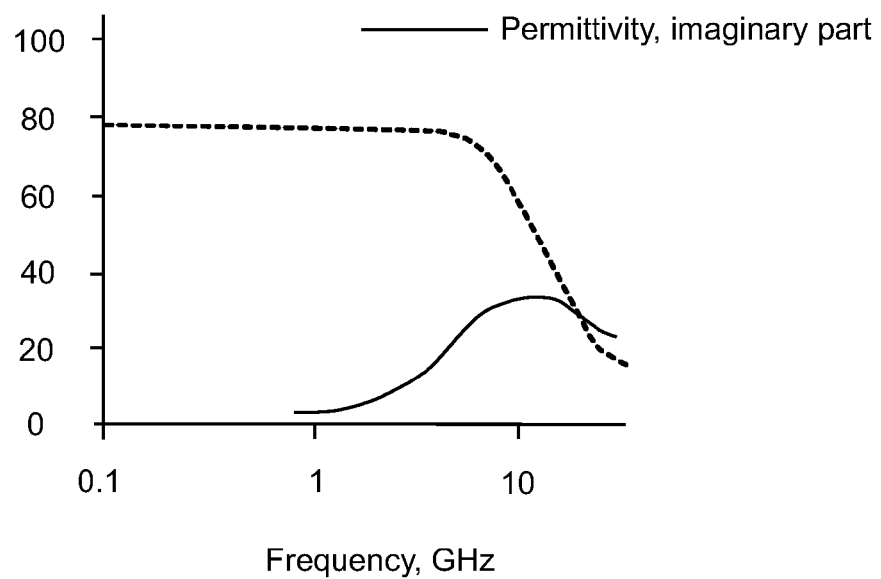
FIG. 5 illustrates an example of permittivity as a function of frequency for water.

Reference may now be had to FIG. 5 illustrating an example of permittivity as a function of frequency of water.

From a comparison of FIGS. 4 and 5, it is recognized that water can be differentiated from oil by using measurements of permittivity as a function of frequency. In addition, it is recognized that the permittivity versus frequency curves in FIGS. 4 and 5 have features such as slopes and changes in slopes that can be characterized by a first derivative and a second derivative. Hence, the first derivative and the second derivative of a permittivity (real and/or imaginary components) versus frequency curve for a formation fluid may be used to estimate a property of the formation fluid.

Figure 6:
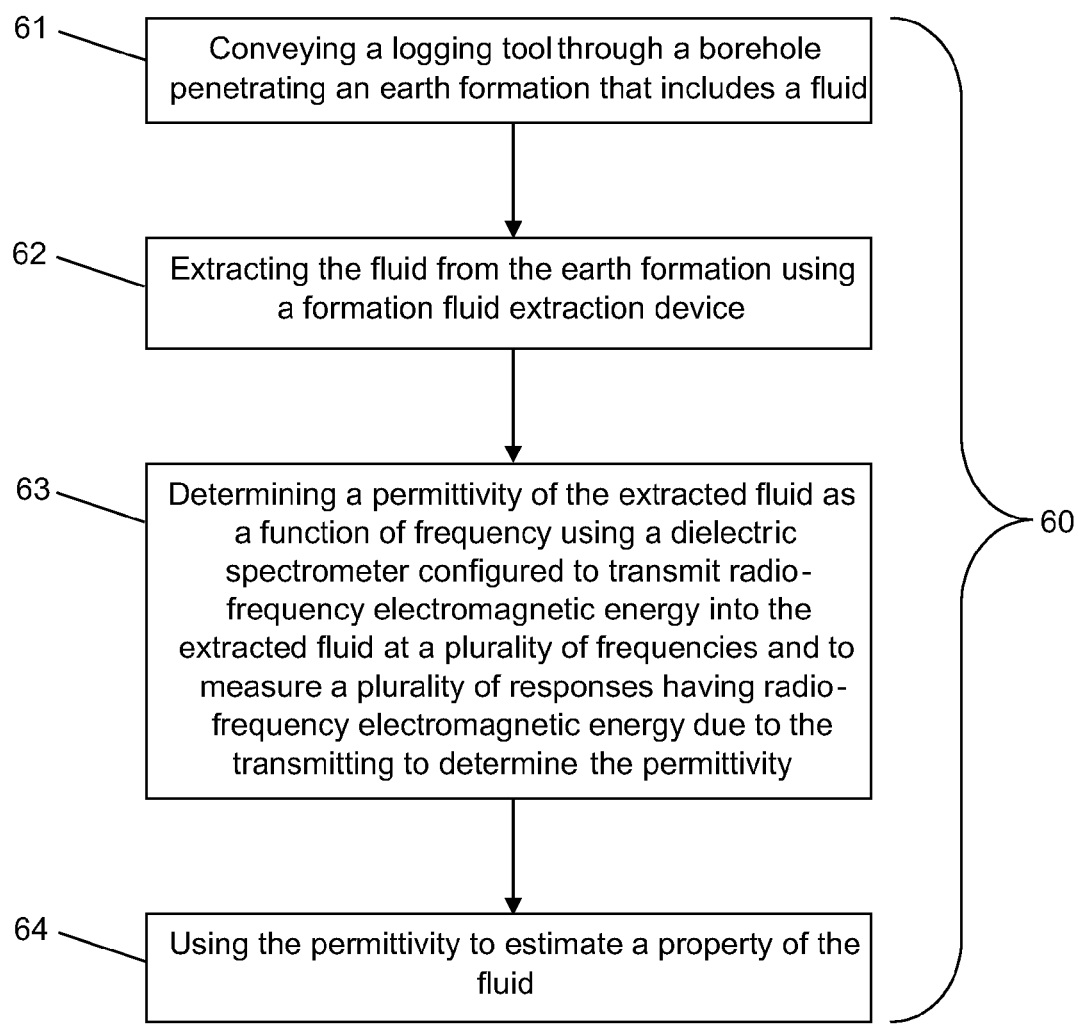
FIG. 6 presents one example of a method for estimating a property of a fluid in the earth formation.

FIG. 6 presents a method 60 for estimating a property of a fluid in the earth formation 4. The method 60 calls for (step 61) conveying the logging tool 10 through the borehole 2 penetrating the earth formation 4. Further, the method 60 calls for (step 62) extracting the fluid from the earth formation 4 using the formation fluid extraction device 6. Further, the method 60 calls for (step 63) determining a permittivity of the extracted fluid as a function of frequency using the dielectric spectrometer 7 configured to transmit radio-frequency electromagnetic energy into the extracted fluid at a plurality of frequencies and to measure a plurality of responses having radio-frequency electromagnetic energy due to the transmitting to determine the permittivity. Further, the method 60 calls for (step 64) using the permittivity to estimate the property.

In support of the teachings herein, various analysis components may be used, including a digital and/or an analog system. For example, the downhole electronics 8 or the surface processing system 9 may include the analog or digital system. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample pump, power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

A "downhole fluid" as used herein includes any gas, liquid, flowable solid and other materials having a fluid property. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof.

The term "carrier" as used herein means any device, device component, combination of devices, media and/or member that may be used to convey, house, support or otherwise facilitate the use of another device, device component, combination of devices, media and/or member. The logging tool 10 is one non-limiting example of a carrier. Other exemplary non-limiting carriers include drill strings of the coiled tube type, of the jointed pipe type and any combination or portion thereof. Other carrier examples include casing pipes, wirelines, wireline sondes, slickline sondes, drop shots, bottomhole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The terms "first" and "second" are used to distinguish elements and are not used to denote a particular order.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. An apparatus for estimating a chemical identity of a downhole fluid, the apparatus comprising:
a carrier configured to be conveyed through a borehole penetrating the Earth;
a downhole fluid extraction device disposed at the carrier and configured to extract the downhole fluid;
a dielectric spectrometer disposed at the carrier and configured to transmit electromagnetic energy into the extracted downhole fluid at a plurality of frequencies and to measure a plurality of responses to determine a permittivity of the extracted downhole fluid as a continuous function of frequency; and
a processor configured to estimate the chemical identity using the permittivity of the extracted downhole fluid as a continuous function of frequency.

2. The apparatus of claim 1, wherein the plurality of frequencies of the transmitted electromagnetic energy is in a radio-frequency range.

3. The apparatus of claim 1, wherein the downhole fluid is extracted from an earth formation.

4. The apparatus of claim 1, wherein the chemical identity comprises at least one selection from a group consisting of oil, water and gas.

5. The apparatus of claim 1, wherein the processor is further configured to estimate a location of a boundary between layers of the earth formation.

6. The apparatus of claim 1, wherein the dielectric spectrometer comprises a test cell configured to receive the extracted fluid and to perform the permittivity measurement.

7. The apparatus of claim 1, wherein the dielectric spectrometer comprises at least one transducer configured to transmit radio waves into the extracted fluid at the plurality of frequencies and/or to receive radio waves as the plurality of responses.

8. The apparatus of claim 1, wherein the plurality of frequencies comprises a plurality of discrete frequencies.

9. The apparatus of claim 1, wherein the plurality of frequencies is provided by a continuous sweep of frequencies.

10. The apparatus of claim 1, wherein the carrier is configured to be conveyed by at least one selection from a group consisting of a wireline, a slickline, a drill string, and coiled tubing.

11. The apparatus of claim 1, wherein the downhole fluid comprises crude oil and the processor is further configured to indicate an amount of asphaltenes in the crude oil.

12. The apparatus of claim 6, wherein the test cell comprises a first electrode and a second electrode configured to contact the extracted fluid in the receiver, the first electrode and the second electrode being further configured to apply a voltage at a frequency and to measure the response.

13. The apparatus of claim 6, wherein the permittivity measurement is performed on a batch of the extracted fluid in the test cell.

14. The apparatus of claim 6, wherein the permittivity measurement is performed on a continuous flow of the extracted fluid through the receiver.

15. The apparatus of claim 7, wherein the at least one transducer comprises a coil.

16. The apparatus of claim 11, wherein the processor is further configured to classify a quality of the crude oil using the indicated amount of asphaltenes in the crude oil.

17. The apparatus of claim 12, wherein the response comprises at least one of in-phase current and out-of-phase current with respect to the applied voltage.

18. The apparatus of claim 14, wherein a rate of the flow of the extracted fluid is selected to prevent a value of the property estimated from changing to another value within a selected interval of time.

19. A method for estimating a chemical identity of a downhole fluid, the method comprising:
conveying a carrier through a borehole penetrating the Earth;
extracting the downhole fluid from within the Earth using a downhole fluid extraction device disposed at the carrier;
determining a permittivity of the extracted downhole fluid as a continuous function of frequency using a dielectric spectrometer disposed at the carrier and configured to transmit electromagnetic energy into the extracted downhole fluid at a plurality of frequencies and to measure a plurality of responses comprising electromagnetic energy due to the transmitting to measure the permittivity; and
estimating the chemical identity with a processor using the permittivity as a continuous function of frequency.

20. The method of claim 19, wherein estimating comprises taking a first derivative of the permittivity as a continuous function of frequency to estimate the property.

21. The method of claim 19, wherein estimating comprises taking a second derivative of the permittivity as a continuous function of frequency to estimate the property.

22. The method of claim 19, wherein the downhole fluid comprises crude oil and the method further comprises indicating an amount of asphaltenes in the crude oil.

23. The method of claim 22, further comprising classifying a quality of the crude oil using the indicated amount of asphaltenes in the crude oil.

24. A non-transitory computer-readable storage medium containing computer-executable instructions stored therein for estimating a chemical identity of a downhole fluid by causing a computer processor to perform:
transmitting electromagnetic energy into the downhole fluid at a plurality of frequencies;
measuring a plurality of responses comprising electromagnetic energy due to the transmitting to determine a permittivity of the fluid as a continuous function of frequency; and
estimating the chemical identity using the permittivity as a continuous function of frequency.

* * * * *